United States Patent [19]
Dutertre et al.

[11] 3,934,140
[45] Jan. 20, 1976

[54] X-RAY DIAGNOSTIC APPARATUS IN PARTICULAR FOR EXAMINING THE INJURED

[75] Inventors: Christian Dutertre; Jean Daugé, both of Argueil, France

[73] Assignee: Establissements Dutertre, Paris, France

[22] Filed: Oct. 9, 1974

[21] Appl. No.: 513,511

[30] Foreign Application Priority Data
Oct. 12, 1973 France .............................. 73.36611

[52] U.S. Cl. ................ 250/320; 250/445; 250/470; 250/490
[51] Int. Cl.².......................................... G03B 5/17
[58] Field of Search ........... 250/439, 445, 446, 456, 250/490, 523, 320

[56] References Cited
UNITED STATES PATENTS

| | | | |
|---|---|---|---|
| 2,281,931 | 5/1942 | Frank................................. | 250/446 |
| 3,670,163 | 6/1972 | Lajus.................................. | 250/320 |
| 3,751,028 | 8/1973 | Scheininger........................ | 250/439 |
| 3,757,118 | 9/1973 | Hodge et al. ........................ | 250/446 |
| 3,803,418 | 4/1974 | Holstrom ............................ | 250/490 |

*Primary Examiner*—James W. Lawrence
*Assistant Examiner*—B. C. Anderson
*Attorney, Agent, or Firm*—Cushman, Darby & Cushman

[57] ABSTRACT

An X-ray diagnostic apparatus intended in particular for the examination of the injured comprising: an X-ray tube-carrying arm member and a film-handling device which are respectively carried by two coaxial shafts, the common axis of which passes through the plane of the film. A horizontal patient-supporting plate is carried by means of an arrangement which enables the plate to be moved longitudinally, transversely and vertically and to be swung about a first vertical shaft, this arrangement being connected to the framework which supports the coaxial shafts in such a way as to enable it to swing about a second vertical shaft the axis of which intersects at the center of the exposure field with both the common axis and the central X-ray beam.

5 Claims, 6 Drawing Figures

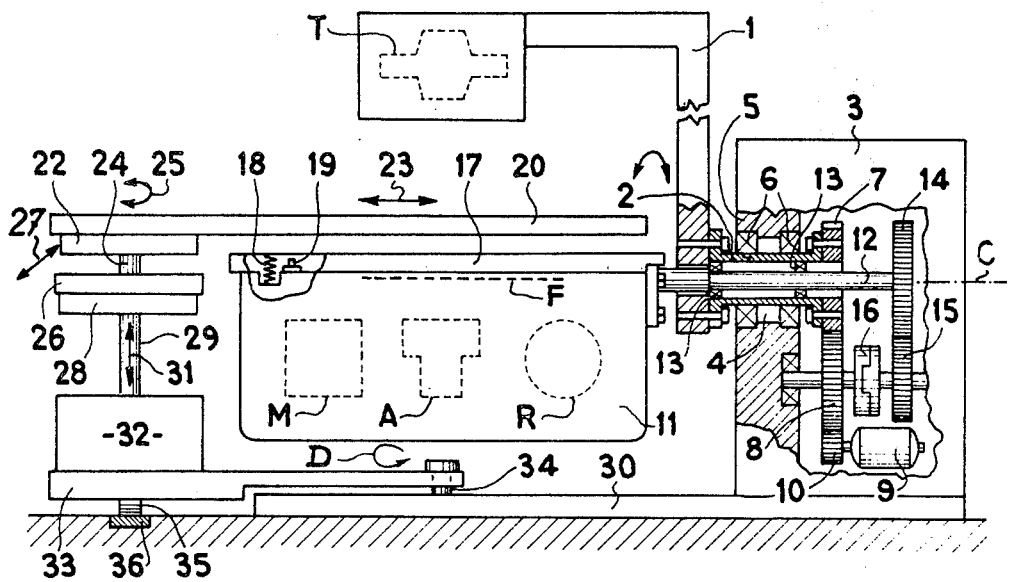
FIG. 1
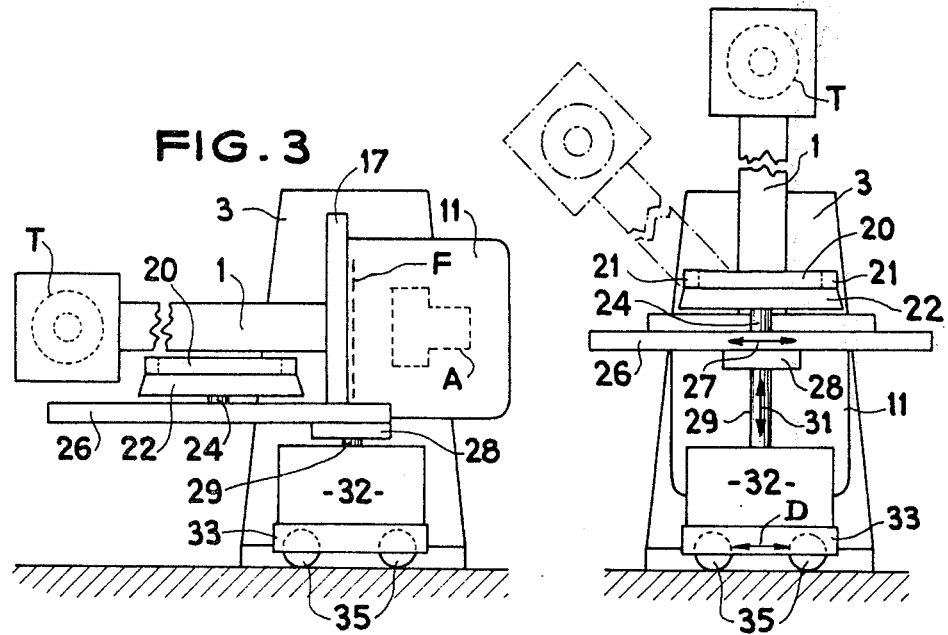
FIG. 3
FIG. 2

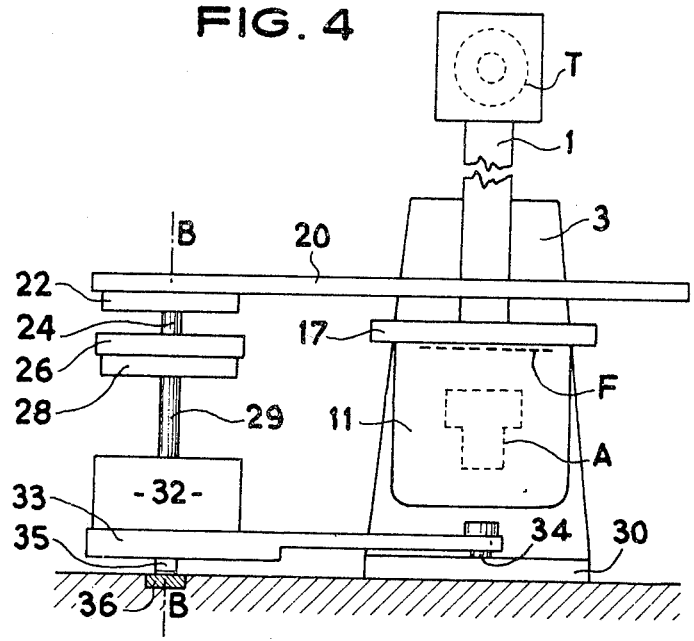
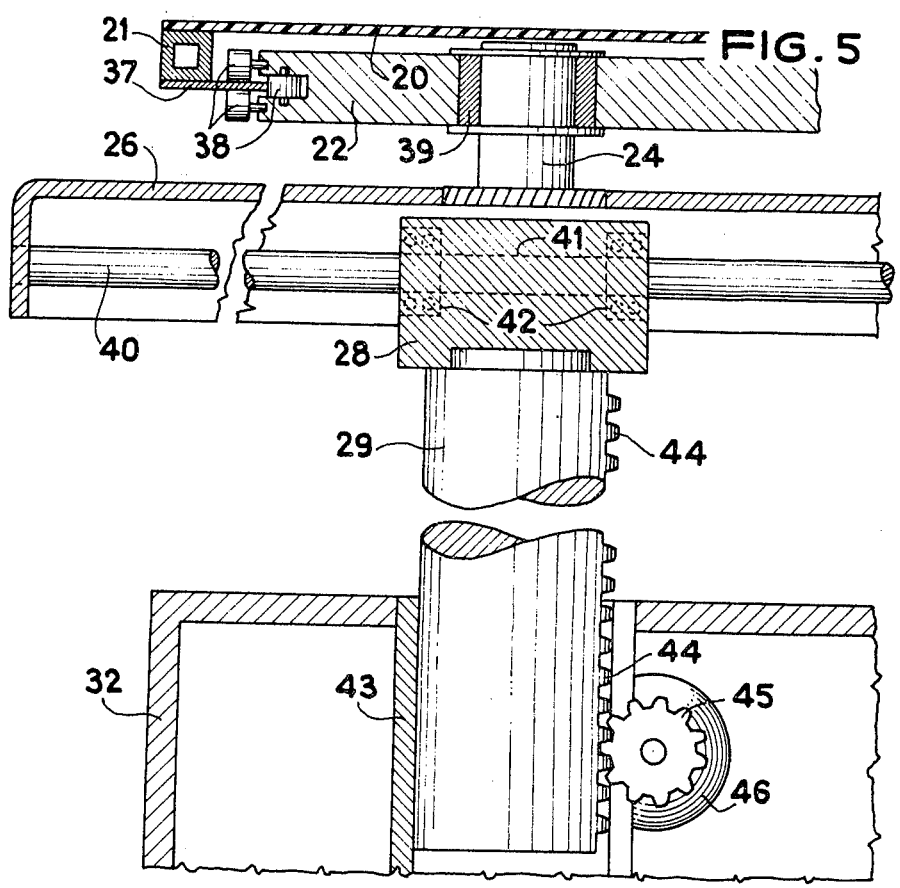

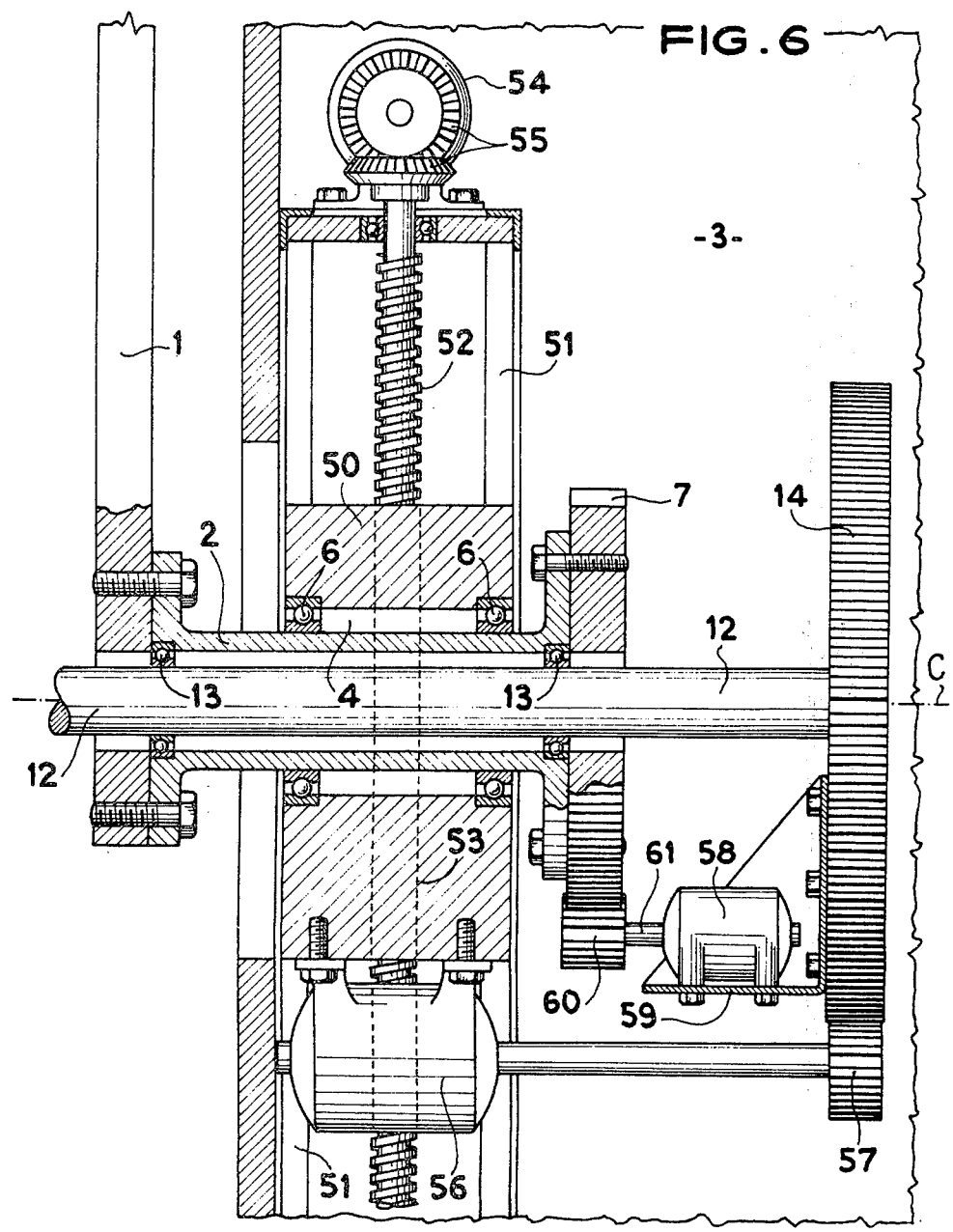

X-RAY DIAGNOSTIC APPARATUS IN PARTICULAR FOR EXAMINING THE INJURED

FIELD OF THE INVENTION

The present invention relates to X-ray diagnostic apparatus intended in particular for the radiological examination of the injured, in which the various parts of the body may be brought within the examination area without moving the patient on his horizontal support.

BRIEF DESCRIPTION OF PRIOR ART

Prior art apparatus for examining the injured employs, for example, a fixed horizontal support for the patient and a support for the X-ray tube which is in the form of a semicircular arcuate arm which may be moved parallel to the axis of the patient and which may pivot about a horizontal axis. Such apparatus has the drawback that it is necessary to move the arcuate arm along the patient to examine the various parts of his body, which gives rise to difficulties at certain angles of incidence and to loss of time when readjusting and which also makes it necessary to turn the patient over on the support so as to examine him on the side opposite from that first examined (left to right or vice versa).

SUMMARY OF THE INVENTION

The present invention enables this shortcoming to be overcome while preserving a very simple and inexpensive form of construction and it has the advantage that it is principally the patient support that is made movable and that it allows the patient's body be fully examined from all directions with minimum movement of the examination equipment. It is thus possible to make a complete survey from the skull to the feet, with or without oblique views, in a very short space of time.

In accordance with the invention, there is provided an X-ray diagnostic apparatus intended in particular for the radiographic and/or radioscopic examination of injured persons, having an arm for carrying an X-ray source and which is in the shape of a quarter-circular arc or a jib and a film-handing device contained in a light-proof housing. The source and film-handling device are respectively supported by means of two horizontal coaxial shafts pivotable individually or together about a common axis which passes through the center of the film plane, the film-handling device being so orientated that the lengthwise movement of the film F is substantially parallel to the common axis. The coaxial shafts are supported in bearings in a rigid supporting frame-work rests on the ground through a fixed plate. A patient-support arrangement is mounted on a movable plate which is pivotable about a first vertical shaft whose axis passes through the center of the X-ray field, and intersects both with the common axis of the coaxial shafts and that of the X-ray beam in a common point of intersection, the first vertical shaft being secured to the fixed plate.

BRIEF DESCRIPTION OF THE DRAWINGS

The invention will be better undestood and other features and advantages will become apparent from the following description, which is given by way of example, and from the accompanying drawings referring thereto, in which:

FIG. 1 is a diagrammatic view in side-elevation of a simplified embodiment of the apparatus according to the invention with the X-ray source and the patient-support means in one of their possible positions;

FIG. 2 is a front-elevational view of the apparatus in the same position as in FIG. 1;

FIG. 3 is a front-elevational view of the apparatus according to the invention with the X-ray source/image-receiver assembly pivoted through 90° with respect to FIGS. 1 and 2;

FIG. 4 is a front-elevational view with the patient-support swung round;

FIG. 5 shows, partly in cross-section, the general details of the patient-support means assembly in an apparatus according to the invention, and FIG. 6 shows, partly in cross-section, a preferred embodiment of the mechanism for controlling the movements of the X-ray source/image-receiver assembly.

DETAILED DESCRIPTION OF THE INVENTION

In FIG. 1, reference numeral 1 refers to an arm member for carrying an X-ray tube which is in the form of an L- or C-shaped bracket or a quarter-circular arc and of which one end carries an X-ray tube T contained in a protective casing (not shown). The other end of the tube-carrying arm member 1 is secured to a first hollow shaft 2, which passes into a supporting framework 3 through a cylindrical opening 4 provided in a rigid vertical wall 5. As a matter of fact, carrying arm member 1 enables the X-ray tube to be positioned at a predetermined distance form its mounting point on shaft 2, this distance having, relatively to the shaft axis, both axial and normal components. The framework 3 is supported on the ground by means of a fixed supporting plate 30. Each end of the opening 4 contains a bearing 6, thus enabling the hollow shaft to rotate about a horizontal axis F. Within the frame 3, the other end of the hollow shaft 2 has secured to it a first gear 7 which enables the shaft to be driven via a second gear 8, by a motor 9 the shaft of which carries a third gear 10.

An image-receiver formed by a film-handling device 11 (which may be of the general type described in U.S. Pat. No. 3,636,351 filed Sept. 19, 1970 to the same assignee or corresponding British Pat. No. 1,318,758) is secured to one end of a second shaft 12 which is mounted inside hollow shaft 2 coaxially therewith. The second shaft 12 is mounted within hollow shaft 2 by means of bearings 13 and its end situated within framework 3 is secured to a fourth gear 14 having the same diameter as the first gear 7 which is mounted on hollow shaft 2. The fourth gear 14 meshes with a fifth gear 15, which is of the same diameter as the second gear 8 and whose shaft is coupled to that of gear 8 by means of, for example, electrically controlled coupling means (clutch) 16. This makes it possible for the motor 9 to drive either only the hollow shaft 2, or the two shafts 2 and 12 together and at the same time, when the X-ray source T is positioned perpendicularly to the plane of film F. This position is indicated by means of, for example, an electrical contact (not shown) which is carried by the hollow shaft 2 and is operated by a cam or a stop (not shown) carried by the second shaft 12 (or vice versa). This contact is connected into the control circuit for coupling means 16 so as to enable gear 15 to be coupled to gear 8 when the contact closes.

Within a light-proof housing, the film-handling device 11 contains, a space for a roll R of film, a group of intensifying screens surrounding film F in the exposure field, a magazine M to store the exposed photographs and an image intensifier A located in the exposure field below the plane of the film F. The film-handling device 11 is mounted on the second shaft 12 in such a way that the common axis C of the two coaxial shafts 2 and 12 passes through the plane of the film F and through the centre of the exposure field as well.

In the area facing the source, the housing containing the film-handling device 11 is covered by a protective lid 17 which is transparent to X-rays and which is mounted on the top of the housing by elastic means such as a set of springs 18 which hold it at a distance from the upper wall of the housing. A set of contacts 19 mounted around the periphery of the upper wall, which are operated when the lid 17 moves towards this wall, are connected into the control circuit (not shown) of the motor 9, thus allowing the pivoting movement of film-handling device 11 to be halted when, for example, the lid 17 strikes the patient supporting plate, which will be described below.

The patient-supporting means, which is shown in greater detail in FIG. 5, comprises a horizontal plate 20 which is intended to receive the patient in a recumbent position. The horizontal plate 20 is provided with a frame consisting of two lateral beams 21 which are able to slide in slide-bearings (not shown in FIGS. 1 to 4) and it may thus move horizontally in translation in the two directions shown by arrow 23, i.e. in parallel to its longitudinal axis. The slide-bearing are carried by a turnable plate 22, which is pivotable through ± 180° about a vertical shaft 24 in the manner indicated by arrow 25; its pivoting movement about shaft 24 enabling the patient to be examined radiographically or radioscopically from head to foot or vice versa without his being moved on the plate 20.

The vertical shaft 24 carrying the turnable plate 22 is in turn carried by an elongated rectangular plate 26 (see FIGS. 1 and 2) which is able to slide perpendicularly to the longitudinal axis of the horizontal patient-supporting plate 20 in the direction shown by arrows 27 (FIG. 2), when the table in the position shown in FIGS. 1 and 2. To this end the elongated plate 26 is provided with sliding runners which fit into fixed seatings or bushings (not shown in FIGS. 1 to 4) which form part of a support block 28 which is small in comparaison with the elongated plate 26 in the direction in which this latter moves. The support block 28 is secured to the upper end of a vertical, cylindrical rod 29 which is movable vertically in the direction shown by arrows 31 by means of a conventional mechanism contained in a pedestal 32. The cylindrical rod 29 may be caused to move vertically by means of a rack and pinion assembly (not shown in FIGS. 1 to 4) or any other type of jack, for example. The pedestal 32 is mounted on a movable second support plate 33, which is capable of swinging through at least ± 90° in the direction show by arrow D about a further vertical shaft 34 which is mounted on the first fixed plate 30 associated with framework 3. The pedestal 32 is secured to the second plate at a distance from said second vertical shaft 34, greater than half the length of the film-handling device housing. The axis of the second shaft 34, when extended, passes through the centre of the plane of the film F, i.e. through the intersection between the common horizontal axis C and the axis of the X-ray beam. The pivoting movement of the support-plate 33 is assisted by rollers 35 which run on a semi-circular track 35 situated at ground level.

FIG. 2 is a front-view of the apparatus shown in FIG. 1 in which an inclined position of the X-ray tube-carrying arm 1 is shown in dashed lines, such a position enables photographs to be taken at an oblique angle (of approximately 45° to the vertical), the plane of the film F being horizontal.

FIG. 3 shows a front-view of the X-ray diagnostic apparatus according to the invention in a position which enables photographs to be taken laterally, i.e. sidewise relatively to the patient. To this end, the sliding plate 26 is brought up against block 28, rod 29 is withdrawn into pedestal 32 (lowered position of patient-supporting plate 20) and the tube-carrying arm 1 and the film-changer 11 are simultaneously pivoted through 90° about the common axis C by engaging coupling means 16 before starting the motor 9.

FIG. 4 is a front-view of the apparatus according to the invention, when the movable plate 33 bearing the pedestal 32 has been swung through 90° about the vertical shaft 34 from the position shown in FIGS. 1 and 2.

Considered as whole, the movements of the apparatus which are described above and shown in FIGS. 1 to 4 enable an injured patient lying on the support 20 to be examined radiographically or radioscopically, from head to foot, at various angles to the vertical and to the longitunal axis of the patient, and they further enable any part requiring detailed examination to be centered relatively to the exposure field by moving the horizontal patient-supporting plate 20 by translatory movement in two perpendicular directions (longitudinal and transverse with respect to the patient) and the respective pivotings of the patient-supporting plate 20 about one vertical shaft 24 and of the movable support plate 33 about another vertical shaft 34.

FIG. 5 shows, partly in cross-section along line B—B of FIG. 4, details of an embodiment of the patient-supporting means. The horizontal patient-supporting plate 20, made of a material which is transparent to X-rays, is bordered at the edge by tubular beams 21 of square cross-section. On their underside, these beams 21 carry guide-strips 37 fitting into sets of three rollers 38, which are mounted on either side of the turnable plate 22. These sets of rollers 38 maintain the table 20 in a fixed position perpendicularly to its longitudinal axis and allow it to be moved parallel to this axis. At the center, the turnable plate 22 has a cylindrical seating 39, into which fits the first vertical shaft 24 about which the turnable plate 22 is able to pivot. The vertical shaft 24 is securely attached to the center of the elongated plate 26, which latter is provided with a device (not shown) for locking the turnable plate 22 at any desired angular position.

The elongated plate 26 contains at least two cylindrical, horizontal rods 40 which are parallel to its longitudinal axis and are arranged symmetrically thereto. The rods 40 pass through cylindrical openings 41 provided in the support block 28 which have at both ends ball-bearing bushings 42 which allow the rods 40 to slide axially within the openings 41. The support block 28 is secured to the top of the vertical rod 29, which latter fits into a cylindrical seating 43 forming part of the pedestal 32. This arrangement allows the displacements of elongated rectangular support plate 26 perpendicularly to a straight line connecting the axis of rod 29 to that of vertical shaft 24. The vertical rod 29 is provided with a rack 44 secured to it and which meshes with a pinion 45 driven by an electric motor 46.

FIG. 6 shows, partly in cross-section, a detail of a preferred embodiment of mechanism for controlling the movements of and for carrying the assembly comprising the X-ray source and the image-receiver (film-handling device 11).

In this embodiment, the assembly formed by the tube-carrying arm 1 and the film-handling device 11 is supported by a carriage 50 in the shape of a parallelepiped slide-block, which is guided by a set of rigid vertical slideways 51 of L-shaped cross-section. The slideways 51 surround the vertical edges of the carriage 50 and allow it to be moved vertically, which is done by means of a threaded rod 52 which engages in an internally threaded bore 53 provided in the body of carriage 50. The threaded rod 52 is driven by a first motor 54, which is fixed with respect to the framework 3, by means of bevel gears 55.

The carriage 50 comprises a cylindrical opening 4, wherein supports through the two bearings 6, the hollow shaft 2 and it also carries a second motor 56 which drives a first pinion 57. Pinion 57 meshes with the gear 14 which is secured to the central shaft 12 which carries the film-handling device 11 and which passes through the hollow shaft 2 in a further pair of bearings 13. A third motor 58, which is mounted on the body of gear 14 by means of a support bracket 59, carries at the end of its shaft 61 a second pinion 60 which meshes with the gear 7 secured to the hollow shaft 2 carrying the arm member 1.

The first motor 54 carries out the vertical movement of carriage 50 by means of gears 55 and the threaded rod 52, and the second motor 56 effects the simultaneous pivoting movement of the two coaxial shafts 2 and 12, when the shaft 61 of the third motor 59 has been immobilised for example, by inserting a non-reversible reduction gear (not shown) between shaft 61 and the second pinion 60, and the third motor 59 effects the pivoting movement of hollow shaft 2, and consequently that of the tube-carrying arm 1 with respect to the central shaft 12, thus enabling the X-ray beam to strike the plane of the film F obliquely.

The X-ray diagnostic apparatus according to the present invention is principally intended for the radioscopic and radiographic examinations of injured persons since it enables patients to be examined from head to foot by manoeuvring the support table longitudinally, laterally, vertically and by swinging it about a vertical axis passing through the centre of the film, without the patient being moved on the table, the plane of which in any position is always parallel to its plane in any other position.

What is claimed is:

1. An X-ray diagnostic apparatus particularly intended for examining injured patients, comprising:
    an X-ray source for emitting an X-ray beam;
    a film-handling device for receiving said X-ray beam traversing said patient, for delivering a visible image thereof and including within a lightproof housing a mechanism for displacing the film it contains in substantially one direction to and from the exposure field irradiated by said X-ray beam;
    an arm member for carrying said X-ray source at one end thereof and for locating said source at a predetermined distance from said exposure field;
    a pair of coaxial, horizontal, independently rotatable shafts having a common horizontal axis, the first one of which having the other end of said arm member secured thereto and the second one supporting said film handling device in such a way that said common axis is located in the plane of the film in the exposure field and that said direction of film displacement is parallel to said common axis;
    a framework including a mechanism for driving said coaxial shaft pair and for supporting it through a cylindrical opening thereof by means of bearings;
    a first supporting plate fixed to the ground for carrying said framework thereon; and
    means for horizontally supporting a patient mounted on a second, movable supporting plate pivotable about a first vertical shaft secured to said first supporting plate, said first vertical shaft having an axis intersecting, at the center of said exposure field, with both said common axis and the central ray of said X-ray beam.

2. Apparatus as claimed in claim 1, wherein said driving mechanism includes at least one first motor for driving said first horizontal shaft independently in rotation about said common axis and means for coupling said first horizontal shaft to said second one for simultaneously rotating both, when said X-ray source carrying arm member is so orientated that the central ray of said X-ray beam is perpendicular to the film plane in the exposure field.

3. Apparatus as claimed in claim 1, wherein said patient-supporting means comprises a pedestal mounted on said movable second supporting plate at a distance, from said first vertical shafts, greater than half the length of said film-handling device housing; a jack mounted in said pedestal including a vertically movable rod; a support-block secured to the upper end of said rod; an elongated rectangular support plate movably mounted on said block for displacements perpendicular to a straight line connecting together the respective axes of said first vertical shaft and of said rod; a second vertical shaft mounted on said movable elongated plate; a turnable plate pivotably mounted on said second vertical shaft and a horizontal patient-supporting plate mounted on said turnable by means of slide bearings for longitudinal displacements thereof.

4. Apparatus as claimed in claim 2, wherein said framework further includes means for movably supporting both said horizontal coaxial shafts and said driving mechanism thereof including said first motor, made up from a carriage mounted for vertical displacements along a plurality of slideways integral with said framework, said carriage displacements being controlled by means of a second motor.

5. Apparatus as claimed in claim 4, wherein said first motor mounted on said carriage drives a first gear meshing with a second gear secured to said second horizontal shaft; said second gear supporting on its body a third motor coupled by means of gears to said first horizontal shaft, whereby said first motor simultaneously drives both of said horizontal coaxial shafts and said third motor drives the first horizontal shaft relatively to the second one.

* * * * *